(12) United States Patent
Goroshevskiy et al.

(10) Patent No.: US 9,746,444 B2
(45) Date of Patent: Aug. 29, 2017

(54) AUTONOMOUS PIPELINE INSPECTION USING MAGNETIC TOMOGRAPHY

(71) Applicants: Valerian Goroshevskiy, Moscow (RU);
Svetlana Kamaeva, Moscow (RU);
Igor Kolesnikov, Moscow (RU);
Leonid Ivlev, Moscow (RU)

(72) Inventors: Valerian Goroshevskiy, Moscow (RU);
Svetlana Kamaeva, Moscow (RU);
Igor Kolesnikov, Moscow (RU);
Leonid Ivlev, Moscow (RU)

(73) Assignees: Valerian Goroshevskiy, Moscow (RU);
Svetlana Kamaeva, Moscow (RU);
Igor Kolesnikov, Moscow (RU)

( * ) Notice: Subject to any disclaimer, the term of this patent is extended or adjusted under 35 U.S.C. 154(b) by 303 days.

(21) Appl. No.: 14/551,295

(22) Filed: Nov. 24, 2014

(65) Prior Publication Data
US 2016/0146758 A1 May 26, 2016

(51) Int. Cl.
*B63G 8/00* (2006.01)
*G01N 27/82* (2006.01)
(Continued)

(52) U.S. Cl.
CPC ....... *G01N 27/82* (2013.01); *B63G 2008/008* (2013.01); *G01N 17/02* (2013.01); *G01N 27/85* (2013.01)

(58) Field of Classification Search
CPC ... H04B 13/02; Y10S 367/904; Y10S 367/91; B63G 8/001; B63G 2008/004; B63G 8/08; B63G 2008/002; B63G 8/16; B63G 2008/005; B63G 8/00; G01V 1/38; G01V 1/3843; G01V 1/3835; G01V 1/3808; G01V 1/03
See application file for complete search history.

(56) References Cited

U.S. PATENT DOCUMENTS 5,894,450 A * 4/1999 Schmidt ................. H04B 13/02
367/131
6,807,921 B2 * 10/2004 Huntsman ................ B63G 8/08
114/312

(Continued)

*Primary Examiner* — Alesa Allgood
(74) *Attorney, Agent, or Firm* — Nadya Reingand

(57) ABSTRACT

The present invention discloses a device and system for magnetographic analysis of mechanical flaws and defects along structures located underwater for example, metallic pipelines, utilizing an autonomous magnetic tomography method (MTM) apparatus based on the inverse magnetostrictive effect for magnetographic identification, in the form of an array of flexible autonomous undersea vehicle (AUV) torpedo constructions of interconnected elements or pods. The array of AUV torpedo constructions are flexibly linked together so that the device can readily navigate within the contours of pipeline to be inspected using the flow media as propulsion means or alternatively by means of independent motive means without interfering with the system flow. The torpedo construction elements or pods each contain three MTM sensors situated 120 degrees apart on a non-perpendicular cross section arrangement, and perform a variety of independent functions. e.g., data storage data, sensor data memory unit, odometer distance measurements, GPS location, geomagnetic navigation capability.

25 Claims, 8 Drawing Sheets

(51) Int. Cl.
　　　*G01N 27/85*　　　(2006.01)
　　　*G01N 17/02*　　　(2006.01)

(56) References Cited

U.S. PATENT DOCUMENTS

| | | | | |
|---|---|---|---|---|
| 6,854,410 | B1* | 2/2005 | King | B63G 8/001 114/244 |
| 7,854,569 | B1* | 12/2010 | Stenson | B63G 8/001 114/322 |
| 2013/0027029 | A1* | 1/2013 | Goroshevskiy | G01S 19/49 324/228 |
| 2015/0063916 | A1* | 3/2015 | Lazzarin | E02F 5/04 405/159 |

* cited by examiner

AUTONOMOUS PIPELINE INSPECTION USING MAGNETIC TOMOGRAPHY

CROSS-REFERENCE TO RELATED APPLICATIONS

This application is a continuation-in-part, and incorporates fully by reference, of U.S. patent application Ser. No. 14/242,938 filed Apr. 2, 2014 claiming priority to U.S. Provisional Patent application No. 61/807,378, filed Apr. 2, 2013. The present application also claims priority to U.S. patent application Ser. No. 13/662,427, filed Oct. 27, 2012; now U.S. Pat. No. 8,447,532; and U.S. patent application Ser. No. 13/674,118 filed Nov. 12, 2012; now U.S. Pat. No. 8,542,127 and incorporate fully by reference.

BACKGROUND OF THE INVENTION

Field of the Invention

This invention relates to underwater measurements, and particularly to pipeline inspection using an autonomous underwater vehicle (AUV) for monitoring of ground, underground, and subsea structures and facilitating inspection or other operations performed on or near the structures. The invention further relates to surveying the condition of ground, underwater and underground structures for maintenance scheduling on said structures.

Background of the Invention

The major causes of pipeline failures around the world are external interference, and defects in metal such as corrosion and cracks—in combination with the stress they experience; therefore, assessment methods are needed to determine the severity of such defects (taking into account the mechanical stress) when they are detected in pipelines. Pipeline integrity management is the general term given to all efforts (design, construction, operation, maintenance, etc.) directed towards ensuring continuing pipeline integrity.

When carrying out an inspection, all prior art autonomous underwater vehicles (AUVs) must be designed to follow an appropriate subsea structure within a close proximity in order to provide useful and accurate information. Typically, At/Vs carry various types of equipment to form images of a surveyed underwater structure. Such equipment typically implements either a sonar technology or visual imaging. MA's can normally follow the structure autonomously, without any needed help from an external operator.

The prior art primarily consists of surveying and inspection facilities limited to inspection operations on pipeline metallic surfaces by inspection means external to the underwater pipeline. It is limited to detection of an obvious bole m the pipe leading to the product (oil or gas) leakage or detection of the free sagging. If the defect is not a through-hole or if the pipeline is placed under ground, an additional means are required to identify the defect.

The present invention addresses prior art problems including, but not limited to, (1) sensor positioning, (2) AUV operation control, during, underwater pipeline inspection, and (3) inspections performed directly inside the pipeline either underwater pipeline, underground or the pipeline at the surface.

SUMMARY OF THE INVENTION

An autonomously driven device is disclosed whereby the device is positioned inside an undersea pipeline, or a land based pipeline in such a manner that uses magnetic tomography features to perform integrity management of surveyed pipeline structures.

The autonomously driven device comprising at least one set of magnetic tomography (MTM) sensors is disclosed. The device is intended for use in a subsea environment to inspect pipelines and other structures located as deep as 1.5 kilometers below sea level. The device comprises an independent power supply, three or more sensors for registering magnetic tomography signals caused by the Earth's magnetic field interacting with defects along a pipeline (known as the Villari effect), a processing unit, and a tracking mechanism. The sensors are arranged in such a way as to avoid overlapping or shadowing if and when the device turns about its axis, and in order to obtain the most accurate reading. The processing unit converts the registered sensor data into a defect distribution map which details the precise 3-D location of defects along the pipeline and the risk associated with each defect.

The autonomous device of the instant invention is configured in a manner of an autonomous undersea vehicle (AUV) in a torpedo construction to inspect pipeline metallic surface outside and inside the pipeline that is flexible and able to navigate internal pipeline bends, different diameters and restrictions, such as joints and tee junctions.

The instant invention provides for an autonomous undersea vehicle (AUV) in a torpedo construction that is flexible and uses magnetic tomography (MTM) sensors in a manner whereby the AUV is adapted to move inside the pipeline to be inspected and has a flexible construction to enable the device to pass readily through pipeline turns, bends, branches.

The AUV apparatus is formed in a series of interconnected pod like elements that provide sufficient flexibility to easily navigate through the internal pipeline contours and can be positioned in a plurality of positions within the pipeline to achieve enough measurable information to map defects in the pipeline metallic surface.

The instant invention utilizes an inspection process that can be passive or active whereby when a magnetic pulse is transmitted the inspection metric measurement is performed and the standard approach of the inventive concept is for a passive mode of operation which implies the pipeline inspection defect metric measurement is caused by a change in the Earth magnetic field.

The instant invention discloses a monitoring unit is designed to assess MTM system performance during scanning metrics, for example, monitored: power level; MTM sensor signals; the longitudinal coordinates of the device; the GPS coordinates of the device, and requirements of the communication system.

The instant invention provides for a plurality MTM sensors within the torpedo elements or pods and positioned spaced apart and configured on perpendicular or non-perpendicular configuration. When there are only three MTM sensors they define a plane and are spaced apart 120 degrees from the adjacent sensor, the defined plane ma or may not be perpendicular to the axis of the pod. When there are more than three MTM sensors the angular distance between each adjacent two sensors is not to exceed 120 degrees.

The instant invention discloses the flexible torpedo array of interconnected elements or pods can be deployed to move autonomously inside a pipeline and is therefore applicable to a) underwater pipelines, b) in ground pipelines, and c) underground pipelines.

Further the instant invention provides for the different torpedo elements or pods to be arranged to perform independent functions, in for example: data storage, odometer, and GPS, located separately from the MTM sensors.

The instant invention provides for a variety of measuring devices (odometer distance measurements) from the start of the inspection process at the entry of the pipeline.

The instant invention includes the provision for special underwater or undersea special location tracking capabilities.

In addition, the instant invention provides for additional torpedo elements or pods with MT sensors for a second series of measurements to improve processing.

In the instant invention the flexible array of torpedo elements of pods is propelled by the pipeline flow media, for example oil flow, and when required with its own motive engine in a manner that does not stop the fluid system operation.

The instant invention provides for the torpedo elements or pods to perform on the basis of non-contact with the pipeline surface and have a plastic cover to preclude collisions within the pipeline.

in addition, the torpedo elements or pods can be provided with wires attached to the external surface of the torpedo element or pod to clean the pipeline surface and to protect against collisions with pipeline walls.

Further in the instant invention the flexible array of torpedo elements or pods are shaped to facilitate motion within the pipeline flow media.

In addition, the instant invention discloses the use of navigation systems in the form of 'geomagnetic navigation system' as alternative to the existing satellite systems such as global positioning system (GPS) and global navigation satellite system (GLONASS) that are dependent on satellite signals.

In addition, the disclosed autonomous ,AUV device in the form of a series of interconnected elements or pods can be deployed in a manner to inspect pipeline metallic surfaces by navigating remotely and externally to the pipeline at a. threshold distance from the pipeline in an undersea environment

BRIEF DESCRIPTION OF THE DRAWINGS

The present invention will now be discussed in further detail below with reference to the accompanying figures in which:

FIG. 3A further details the device, also denoting cross-sections of sensors and the predetermined distances between a MTM signal generator and the sensors.

FIG. 3B shows an example of sensor positioning on a device's outer surface.

FIG. 3C shows an example of sensor positioning on a device's inside surface.

DETAILED DESCRIPTION OF THE PREFERRED EMBODIMENTS

Figure 1:
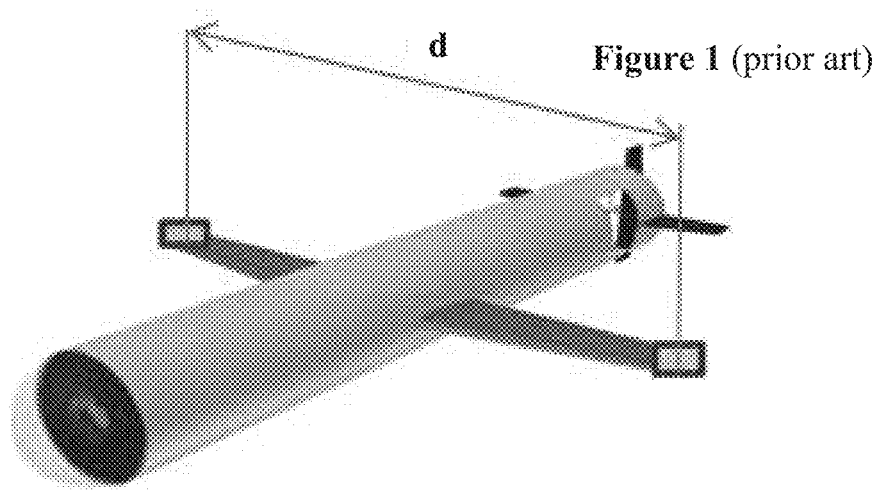
FIG. 1 illustrates a planar positioning of the sensors.

The term "remote," as used herein is defined as being used from a substantial distance from a structure under testing. The term is used to signify that a sensor, as defined herein, is not necessarily located in close proximity to the structure being tested. The preferred embodiment of the invention performs best when the distance between structure and sensors ranges from 1-50 meters, however, the term remote is intended to mean up to 15 times the diameter of the structure being surveyed. This makes the invention especially effective for testing structures located deep underground and underwater.

The term "threshold distance," as used herein, is defined as an amount equal to 15 (fifteen) times the diameter of a structure being surveyed, or scanned. The term is used to describe the range of the device and method claimed herein (i.e. the maximum distance between a given structure and a device during operation).

The term "sensor," or "sensors," as used herein, is defined, as an interconnected sensing unit. The term should be read as a sensing unit comprising three or more magnetic signal, or magnetic tomography (MTM) sensors, which detect the signal caused by the :Earth's magnetic field after it travels through a structure being inspected. Such sensors also detect any artificial MTM signal by an additional MTM signal generator.

The term "memory unit," as used herein, is defined as a module which saves signals registered by the sensors or sensor array to a file as data. The memory unit acts as a step between the sensors and the processing unit.

The term "processing unit," as used herein, is defined as a module which receives MT sensor data (potentially via a memory unit) and further processes the various files to determine (1) the presence of anomalies/defects along a structure, (2) the risk corresponding to each anomaly (e.g., the size/depth of the defect), (3) the three-dimensional location of each anomaly along a structure, and (4) whether the device is maintaining correct positioning in tracking the structure.

The term "magnetic tomography method," or "MTM," as used herein, is defined as a non-contact pipeline surveying method employing detected differences in the magnetic field near a ferro-magnetic structure. The term "MTM sensor" refers to the specific sensor(s) which detect the magnetic field created by (1) the Earth, or (2) the MTM signal generator. The term "MTM signal generator" refers to an additional emitter of an electromagnetic or magnetic signal.

The term "second signal generator," as used herein, is defined as any additional signal emitter according to known methods in the art. Similarly, the term "second sensing, unit" is defined as any additional sensing mechanism according to known methods in the art. The second signal generator and second sensing unit are part of a mechanism of tracking the axis of an underwater structure to ensure that the device is operating along the correct path.

The term "horizontal cross section," as used herein, is defined as the cross section of the body of a device as claimed herein corresponding to a slice perpendicular to the trajectory of the device. For example, if the device were in the shape of a cylinder, a horizontal cross section corresponds to the shape of a circle (and not a rectangle, which would correspond to a vertical cross section of the same cylinder).

The term "array," as used herein, is defined as any configuration of two or more units, wherein the distance between said units is optionally fixed, predetermined, and known. Examples of arrays include but are not limited to equal distances on a line through a central axis point, 2-dimensional configurations, and 3-dimensional configurations of various shapes and sizes The term "odometer," as used herein, is defined as a portable odometer unit, fixable to a main unit (i.e. the apparatus), intended for distance measurement along a route of extended engineering structure such as a pipeline. The odometer facilitates fixing of the linear coordinates of defect areas revealed during in-line, non-contact magnetometric or other diagnostic inspection. The odometer can be used for marking the longitudinal coordinates along an underwater structure axis for compilation of data for a database for certification of each process, and as a unit of a pipeline route-tracer set with a function of laying depth measurement.

The present invention discloses an autonomous magnetic tomography method (MTM) and device for magnetographic identification and magnetographic analysis of mechanical flaws and detects along structures located deep in the sea or otherwise located underground and/or underwater. The invention optimizes the inspection and maintenance processes of extended metallic constructions, e.g., pipelines.

The MTM device is based on the inverse magnetostrictive effect (i.e., the Villari effect)—the variation of a material's magnetic susceptibility under applied mechanical stress. Generally, this technique uses the natural magnetization of a ferrous pipe by the Earth's magnetic field. The changes in magnetic susceptibility result in distribution of a magnetic field gradient along a structure's surface area, thus providing information about (1) the presence, and (2) the value of the magnetic field anomaly at a given and precise location on the structure. In this invention, the device is capable of autonomous and offline operation underwater at depths up to 1,500 meters below sea level.

The device and method disclosed comprise various types of sensor positioning. Some examples are provided below.

The array of remote MTM sensors coupled to the device according to the present invention is capable of localizing coordinates of an underwater structure at any given moment and detecting anomalies of the magnetic field at each localized coordinate along a structure, thus employing a non-contact remote technique based on measuring a value of the Earth's magnetic field at various locations as the device approaches, reaches, and departs from a specific area of the structure. It should be noted that the array of sensors is capable of obtaining 3-dimensional information such that the processing unit can create a 3-dimensional defect distribution map. That is, the device is able to determine the precise location of a defect at a specific area of a surveyed structure (e.g., on the bottom, on left side, on the right side, on the top, etc.).

The remote sensors register information which makes it possible to identify anomalies on and along a structure by measuring the deviation of the Earth's magnetic field at each monitoring location from a control, or background, value, without the need for an additional magnetic field or signal during the measuring process. It is noted, however, that certain embodiments of the present invention do comprise an additional MTM signal generator for signal amplification purposes (see further below).

The remote sensor array is further capable of localizing coordinates of foreign objects in the vicinity of a structure, processing anomaly locations with such foreign objects, and making and recording, a link between the anomaly location and a nearby foreign object and its location.

The use of the AUV device claimed herein does not require any preparation of the pipeline for testing e.g., cleaning, opening the pipe, or stopping pipeline operation. The device is capable of detecting flaws of various types, including but not limited to internal or external corrosion, long crack-like pipeline detects, and welding defects. The use of the device is not limited by features such as a structure's diameter, configuration, or protective coatings, change of pipe diameter or wall-thickness, turning, or twisting pipes, transported product within the pipe (e.g., gas, oil, water), pressure, and pipeline protection (e.g., cathodic protection).

The claimed device evaluates the degree of danger of defects by the level of concentration of mechanical tensions (instead of, e.g., defect geometry (i.e., length-width-depth)), Several methods are disclosed to generate additional signals are proposed by the present invention. Some examples are given here:

In one embodiment, a unified signal is emitted, transmitted, and detected by all sensors. The distance from the generator to the sensors is taken into account. This type of signal permits the AUV unit to analyze the decay rate of the signal associated with the non-homogeneity of a magnetic field line caused by defects inside, outside, or along a structure. This type of signal generation is more cost-effective with regard to power generation. This particular method allows for a more precise adjustment of sensors based on a single level of signal generation (i.e. one signal, rather than more than one), as the generated signal strengthens the (electro)magnetic signal from the structure being scanned (e.g., in the case of a weak natural signal) and decreases the external noise of any potentially interfering objects.

In another embodiment, two or more signals are generated for each particular sensor. The characteristics of each signal generated must be identical to each other, and the distance from the generator to the sensors should be the same. This type of system may be preferable when stronger interference signals exist between a pipeline and third party objects, and/or when it is more difficult to extract a desired signal due to background noise.

In yet another embodiment, the invention discloses a power supply system comprising at least two individual units.

A main power unit provides power for the AUV device. The AUV device powers the MTM signal generator. The power supply required for the performance of the AUV unit is calculated based on the total capacity of every component of the AUV unit.

A second unit, i.e. an independent power unit, is used to back up the main power unit and ensure the integrity of information recorded by the recording unit and the backup storage unit.

Recording and storage of information. A memory unit is designed for safe data storage obtained during, the scanning and analyzing process performed by the AUV device. Recording is carried out either (1) by running the internal clock unit, or (2) by an odometer (which is either coupled to the AUV device or part of an external AUV device/unit). Additionally, information on the longitudinal and GPS or GLONASS coordinates is synchronized with sensor readings, all of which is recorded in a single data file.

Before each individual scan, a new holding data file is created by the device. During the scan, the holding data file is filled with information from the scan until the arrival of a subsequent pulse either (1) from an odometer or (2) from an internal clock.

The claimed device and method continuously records and stores information, further organizing it within an external drive. At shorter distances below sea level, a known communications system may also be provided (e.g., radio, optical, wireless), which allows for control by an operator, as well as a means for transfer of control between an operator (e.g., human) and the AUV device itself—for online, or autonomous, operation. The AUV device can, however, operate in a completely autonomous fashion, surveying structures at depths beyond those where any presently known communications system can reach. In such cases, the claimed device operates alone, collecting the required data while moving along the structure, subsequently returning to the surface or at least a location where communication is once again possible.

The communication system provides the AUV device a connection with additional hardware and software for device operation and maintenance. Such additional hardware and software can be used for, e.g., additional power supply and/or regulation thereof, or a logical and physical interface other on-board systems of the device. A variety of known approaches can be used for an interface and the packet structure transmission and reception (e.g., RS-232, RS-485, Ethernet, CAN, file system and database structure, and DC/AC power).

The instant invention discloses a monitoring unit that is designed to assess MTM system performance during scanning. The following factors, for example, are monitored: power level; sensor signals; the longitudinal coordinates of the device; the GPS or GLONASS coordinates of the device, and requirements of the communication system.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The instant invention utilizes an inspection process that can be passive or active whereby when a magnetic pulse is transmitted the inspection metric measurement is performed and the standard approach of the inventive concept is for a passive mode of operation which implies the pipeline inspection defect metric measurement is caused by a change in the Earth magnetic field.

Figure 2:
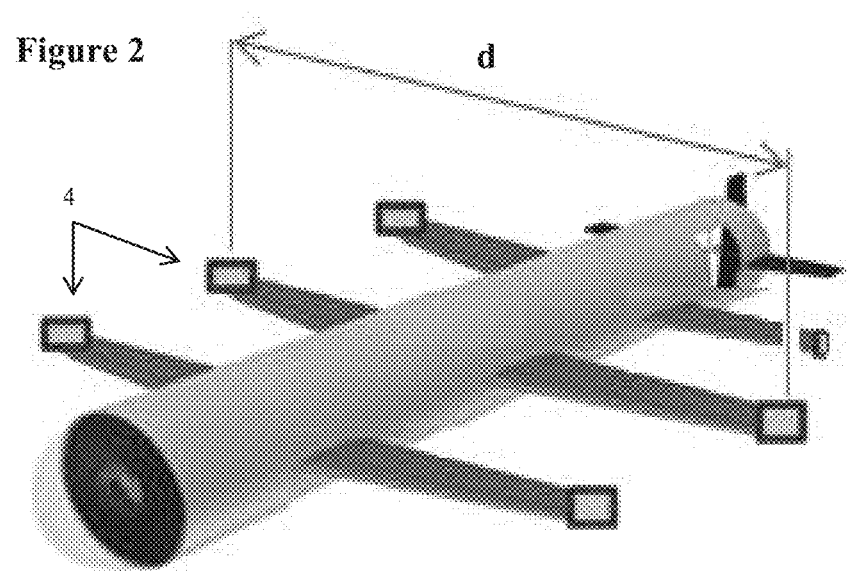
FIG. 2 shows an AUV device coupled, in this example, to three pairs of planar sensors

One embodiment of the present invention comprises a 3D system of sensors registering MTM signals to provide minimum sufficient conditions for MTM inspection of pipelines. The sensor positions 4 can be chosen in a planar manner in FIG. 1, where the distance d between the sensors is selected based on the requirements of particular MTM specifications (see U.S. application Ser. No. 13/662,427 of the same inventors). The number of sets of remote sensor arrays can be more than one (e.g., two, three, four, and so on) as seen in FIG. 2. In this case, two or more sections perform measurement at the same time, thus simultaneously providing individual longitudinal magnetic field gradients. With planar positioning, the distance between the sensors is pre-calculated and predetermined.

Figure 3A:
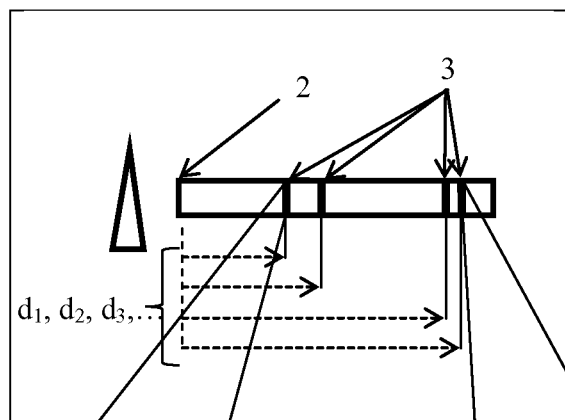
FIGS. 3A, 3B, 3C show an AUV device in more details.
Figure 3B:
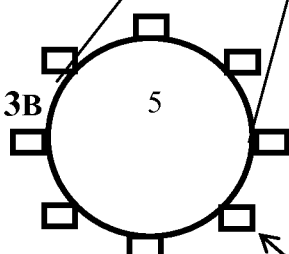
Figure 3C:
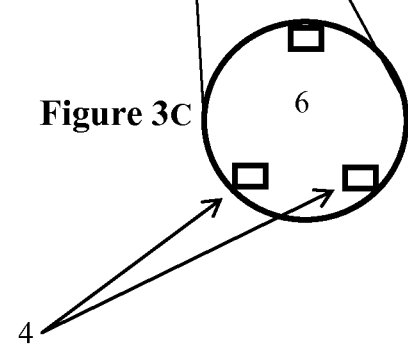

Situations, however, arise where it is impossible to provide a predetermined distance between the sensors (due to, e.g., a limitation of the dynamic characteristics of an AUV). Under such circumstances, the number of sensors 4 is varied and the sensors are positioned in an axial manner, wherein the sensors are arranged at equal distances from a central point. An example of this embodiment is shown in FIGS. 3B and 3C. The sensors are coupled either to the outer surface of an AUV device 5 FIG. 3B, or to the inside surface of the AUV device 6 in FIG. 3C. Multiple sets 3 of axial sensors may be installed on the AUNT device, as shown in FIG. 4A. The distance $d_1$, $d_2$, $d_3$, . . . between these sets of sensors 3 is pre-calculated and predetermined in order to most accurately display the MTM information.

The claimed method and device optionally include a signal generator that produces specific signals, e.g., signals of a specific shape. The processing center of the claimed method and device registers the change of the signal, and the decision of the presence of an anomaly or defect in the pipeline is made based on the change from the generated signal uniformity. The choice of the signal's shape (e.g., its amplitude, phase shift and frequency) is based on the particular pipeline under investigation. This can be adjusted during preliminary testing in the lab or directly onsite.

The signal is generated by a set of magnetic coils being oriented relative to each other in a specific way. Generator output power is determined by the power supply, which is described thither below. The signal generated is emitted by a MTM signal transmitter 2.

Several solutions to generate signals are proposed:

A unified generation of a signal that is detected by all sensors. The distance from the generator to the sensors is taken into account. This type of signal permits the AUV unit to analyze the decay rate of the signal associated with the non-homogeneity of a magnetic field line caused by defects inside, outside, or along a structure.

A signal generation system where the signal generator is set for each section of the sensor. The parameters of the generation must be identical to each other, and the distance from the generator to the sensors should be the same. This type of system is preferable when strong interference signals exist between a pipeline and third party objects, and/or when it is difficult to extract a desired signal due to background noise.

A main power unit provides power for the AUV device. The AUV device power the MTM signal generator 2. The power supply required for the performance of the AUV unit is calculated based on the total capacity of every component of the AUV unit. A second unit, i.e. an independent power unit, is used to back up the main power unit and ensure the integrity of information recorded by the recording unit and the backup storage unit.

Recording and storage of information. A memory unit is designed for safe data storage obtained during the scanning and analyzing process performed by the AUV device. Recording is carried out either (1) by running the internal clock unit, or (2) by an odometer (which is either coupled to the AUV device or part of an external AUV device/unit). Additionally, information on the longitudinal and GPS coordinates is synchronized with sensor readings, all of which is recorded in a single data file.

Before each individual scan, a new holding data tile is created by the device. During the scan, the holding data file is filled with infomiation from the scan until the arrival of a subsequent pulse either (1) from an odometer or (2) from an internal clock.

The claimed device and method continuously records and stores information, further organizing it within an external drive. Any known communications system may also he provided (e.g., radio, optical, wireless), which allows for control by an operator, as well as a means for transfer of control between an operator (e.g., human) and the AUV device itself—for online, or autonomous, operation.

Figure 4:
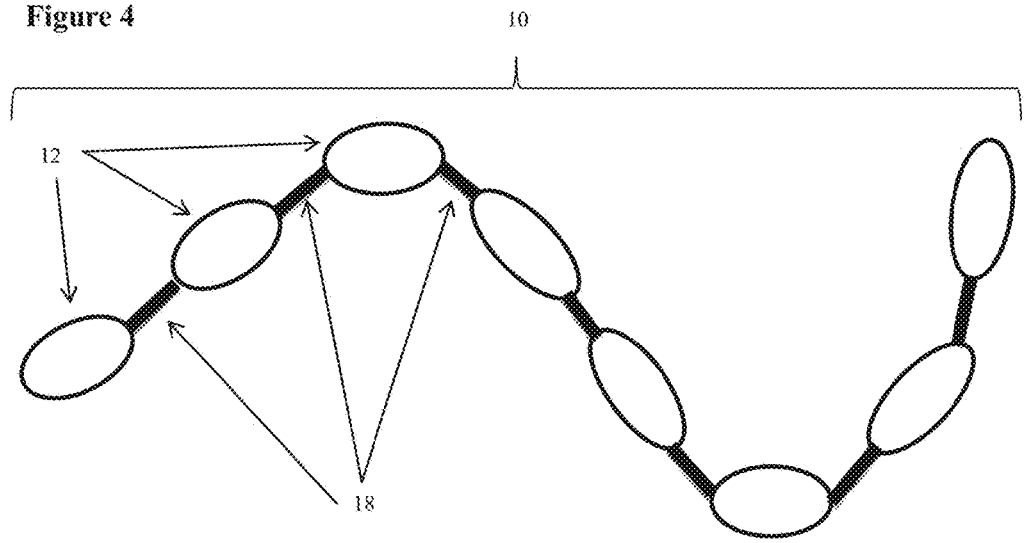
FIG. 4 illustrates an array 10 of interconnected flexible torpedo elements or pods 12 connected by links or connectors 18.

The instant invention specifically discloses a flexible army 10 of torpedo elements or pods 12 as shown in FIG. 4 that are interconnected by rigid links or connectors 18, in a manner that promotes the connected torpedo elements or pods 12 to articulate and move independently of each other through hinged or pivoted means at each end.

Monitoring AUV device performance. A monitoring unit is designed to assess MTM system performance during scanning. The following factors, for example, are monitored: power level; sensor signals; the longitudinal coordinates of the device; the GPS coordinates of the device, and requirements of communication system.

Figure 7:
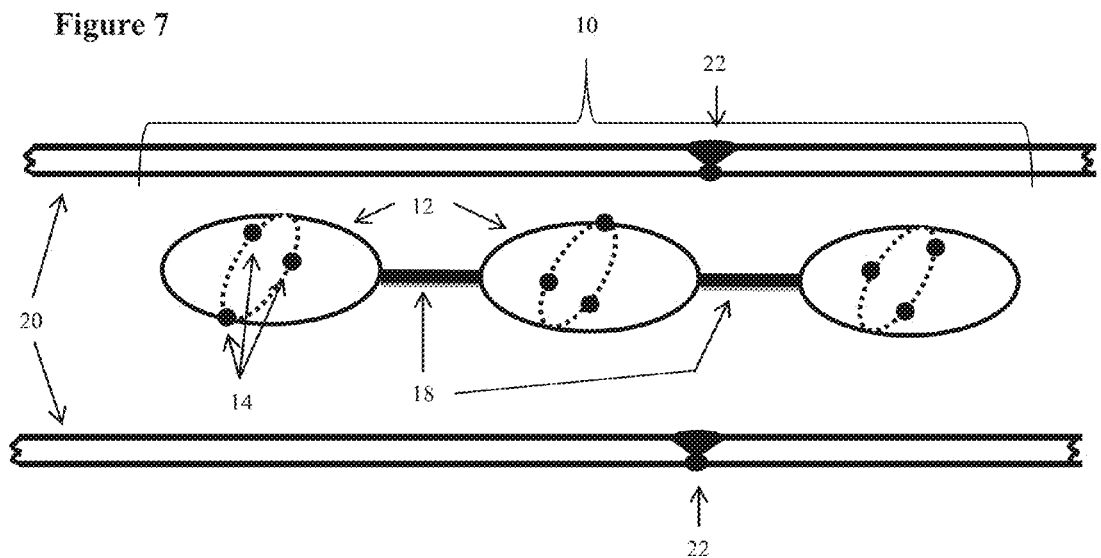
FIG. 7 illustrates the array device 10 for example located inside a submerged metallic pipe structure 20 comprising for example a full penetration butt weld 22 subject to examination.

It will be evident from the information being, provided that the flexible array device 10 is readily placed inside a submerged or in-ground or underground pipeline structure 20 as illustrated in FIG. 7.

Figure 5:
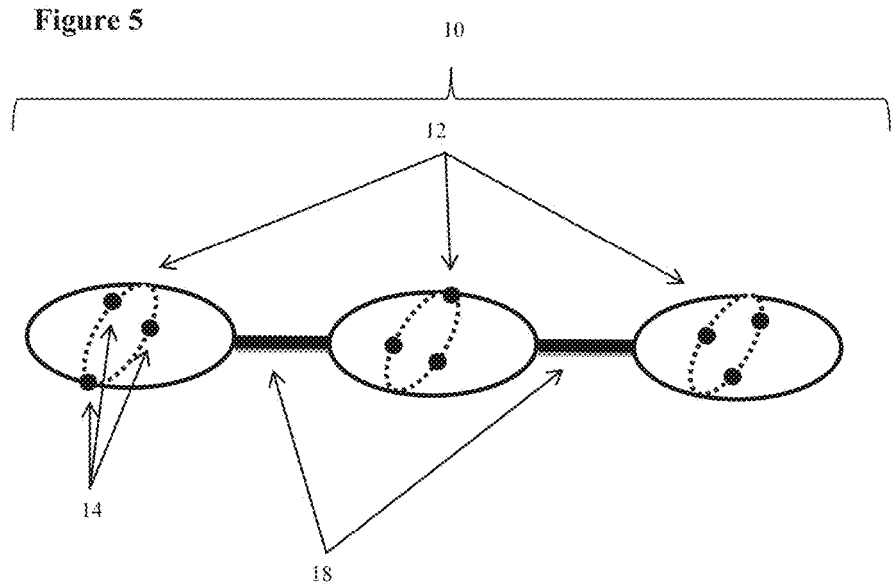
FIG. 5 illustrates an example of the positioning of three MTM sensors 14 within the torpedo element or pod 12 positioned at 120 degree apart on a non-perpendicular cross sectional configuration.

In addition, the instant invention provides for three MTM sensors 14 within the torpedo elements 12 and positioned spaced apart at angles of 120 degrees and configured on perpendicular or non-perpendicular configuration as illustrated in FIG. 5. The configuration is non-perpendicular to the axis of the torpedo elements or pods 12. A plurality of MTM sensors 14 are used. When using more than three MTM sensors 14 the sensors should be positioned such that two adjacent sensors are separated by no more than an angular distance of 120 degrees.

Further in the instant invention, the MTM sensors 14 are of a rigid construction.

In the instant invention the flexible torpedo array 10 can be deployed to move autonomously inside a pipeline as is therefore applicable to a) underwater pipelines, b) in ground pipelines, and c) underground pipelines.

The instant invention locates the MTM sensors 14 at 120 degree spaced apart angles and on a non-perpendicular pipeline cross-section in a manner to achieve complete information to map pipeline surface metallic defects.

Further the instant invention provides for the different torpedo elements 12 to be arranged to perform independent functions, in for example, data storage data, memory storage, distance odometer, and GPS or GLONASS systems, and based on separate inputs from the MTM sensors 14.

In addition, the instant invention provides for additional torpedo elements 12 with MTM sensors 14 for a second series of measurements to improve processing of data information.

Figure 10:
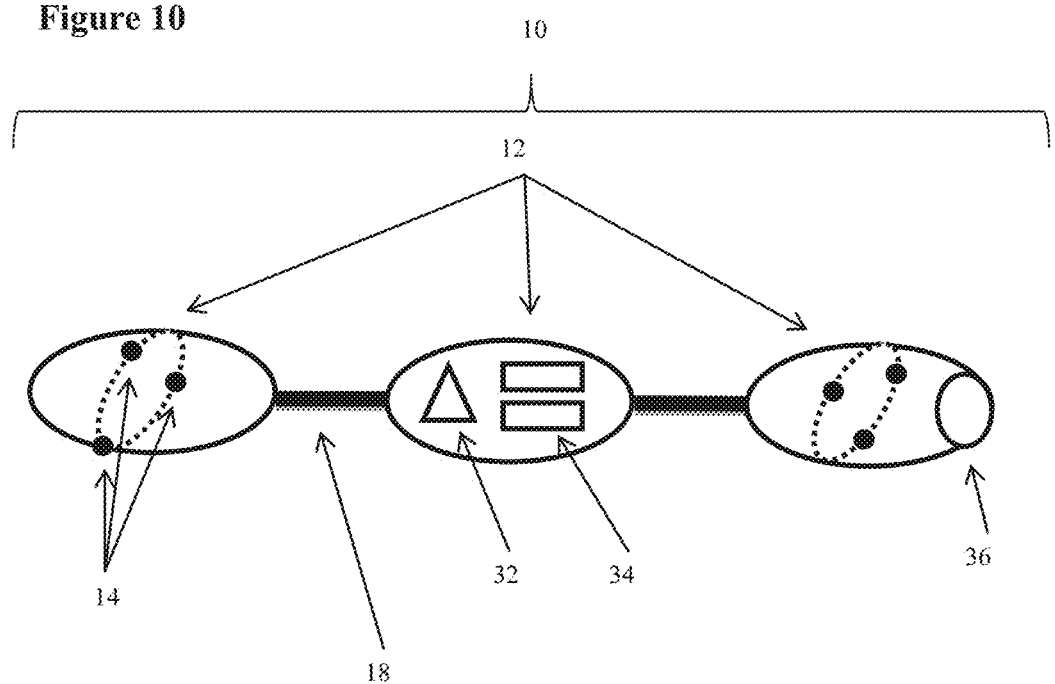
FIG. 10 illustrates additional system configurations of the torpedo elements or pods 12 of the array device 10.

In the instant invention the flexible array 10 is propelled by the pipeline flow media, for example oil flow, and when required with its own motive engine 36 in FIG. 10 without interrupting the fluid media flow systems.

In addition, the instant invention provides for the flexible array 10 to move flexibly inside the pipeline to navigate turns, bends, branches and couplings that are part of the pipeline structure 20 construction.

The instant invention provides for the torpedo elements 12 perform on the basis of non-contact with the pipeline surface and have a plastic cover to preclude collisions within the pipeline.

Figure 6A:
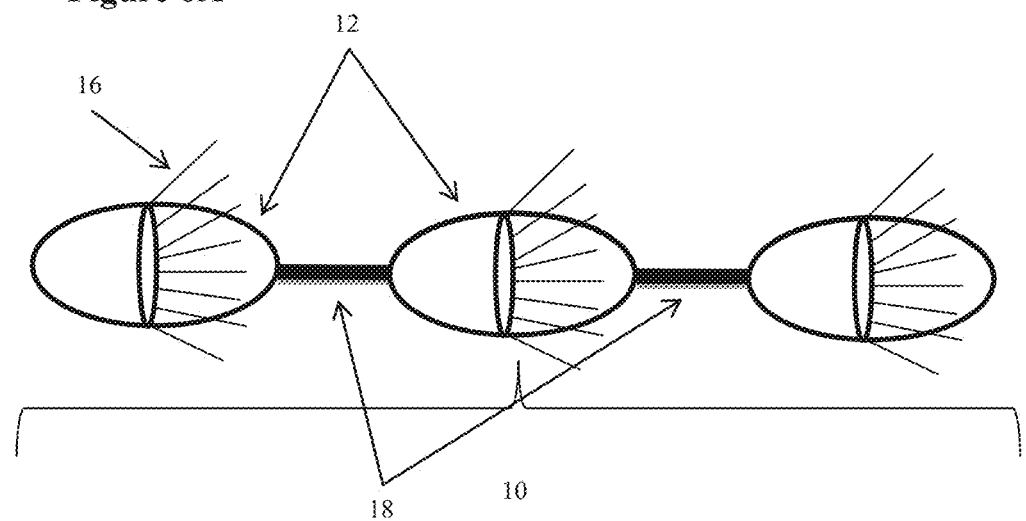
FIGS. 6A and 6B illustrates the torpedo elements or pod 12 with external wires 16.
Figure 6B:
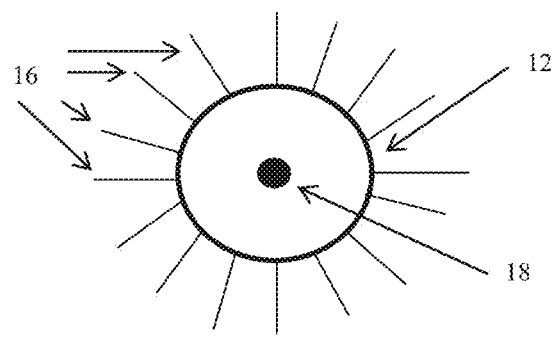

In addition, the torpedo elements 12 can be provided with wires 16 as illustrated in FIGS. 6A and 6B attached to the external surface to clean the pipeline surface and to protect against collisions with pipeline walls.

Further in the instant invention the flexible array 10 and torpedo elements are shaped to facilitate motion within the pipeline flow media, as shown in FIG. 7 disclosing a submerged pipeline 20 by sensing the pipeline magnetic measurement properties as shown and subject to examination of for example, a full penetration butt weld 22.

In yet another embodiment, the invention discloses a power supply system for transporting the flexible array 10 and comprising at least two energy source individual units 34 in FIG. 10.

In addition in a further invention embodiment, the instant invention discloses the use of navigation systems 32 in FIG. 10 in the form of geomagnetic navigation system as alternative to existing satellite systems such as GPS and GLONASS that require satellite system support.

The stated geometric, magnetic system is a passive autonomous navigation technique that can be implemented in at least two ways, a) by use of geomagnetic matching, and b) geomagnetic filtering.

Figure 9:
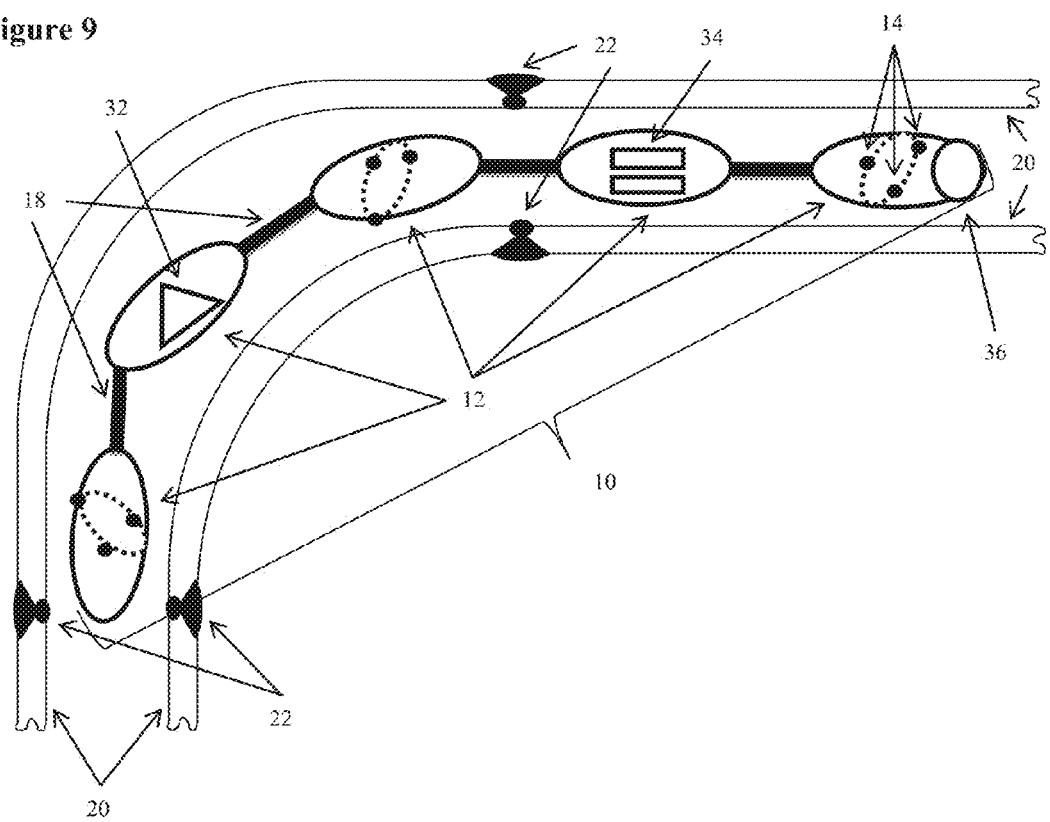
FIG. 9 illustrates the array device 10 for example located inside a metallic pipe structure 20 with a bend comprising for example penetration butt welds 22 subject to examination.

FIG. 9 demonstrates the flexible array device's 10 ability to navigate a bend in a pipe while with multiple torpedo elements or pods 12 serving different functions. The links between the elements allow to perform turns of 90 degrees or even more.

Figure 11:
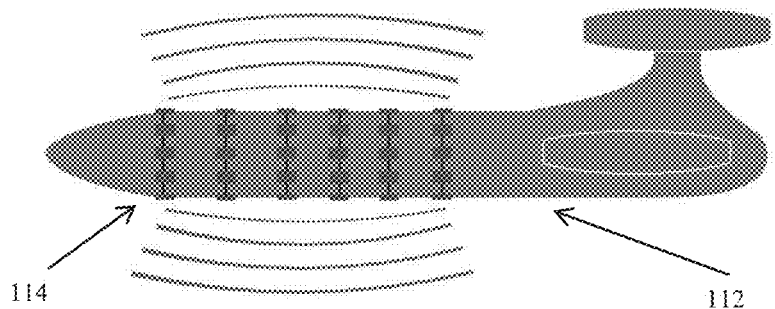
FIG. 11 illustrates rust the torpedo element 112 and sensor rings 114.

FIG. 11 shows the torpedo element 112 surrounded by sensor rings 114.

Figure 12:
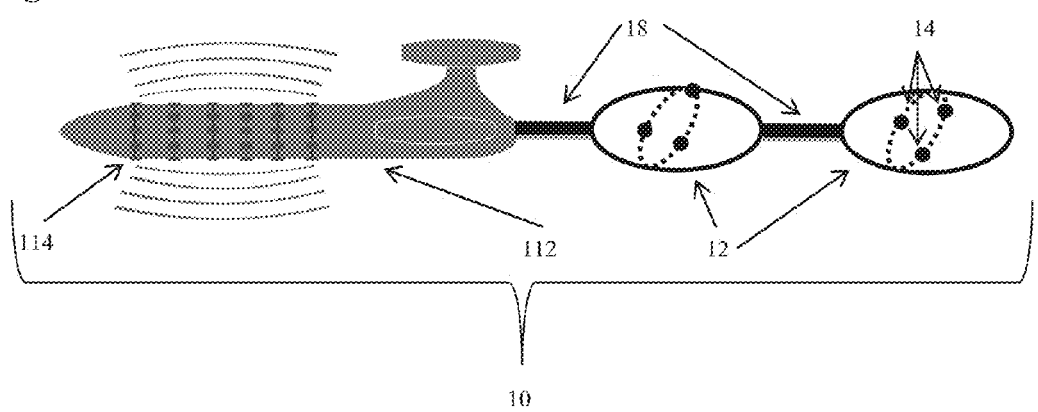
FIG. 12 illustrates the torpedo element 112 connected to pods 12 by connectors 18.

FIG. 12 shows the torpedo element 112 attached to pods 12 by connectors 18 allowing for greater flexibility of the array device 10. Pods 12 include non-perpendicular MTM sensors 14.

The principle of geomagnetic matching and geomagnetic filtering uses algorithms for measurement equations by the surface Spline method incorporating MAD (mean absolute difference) and EKF (extended Kalman filter) simulations, and in practice improves efficiency of navigation systems.

The instant invention provides for a variety of measuring devices (odometer distance measurements) from the start of the inspection process at the entry of the pipeline.

Figure 8:
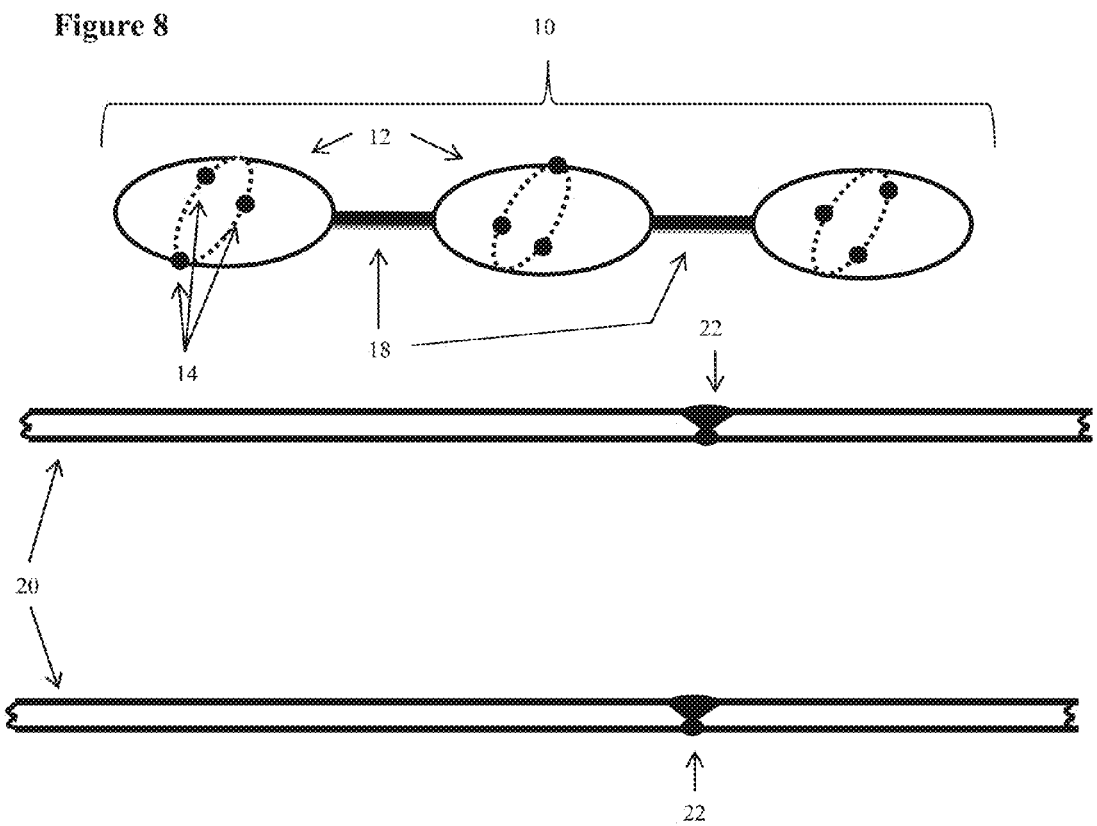
FIG. 8 illustrates the array device 10 for example located external to submerged metallic pipe comprising for example a full penetration butt weld 22 subject to examination.

The instant invention in a further embodiment enables the flexible array device 10 to provide information relating to the location and position of the pipeline to be inspected when the flexible any device 10 is not inside the pipeline, but for example, moving in the vicinity of the pipeline 20 underwater or undersea by sensing the pipeline magnetic measurement properties of for example, a full penetration butt weld 22 as shown in FIG. 8.

The instant invention includes the provision tor special underwater or undersea special location tracking capabilities.

In addition, in yet a further invention embodiment, the disclosed autonomous AUV device 10 in the form of a series of interconnected elements or pods 12 can be deployed in a manner to inspect pipeline metallic surfaces by navigating remotely and externally to the pipeline at a threshold distance front the pipeline in an undersea environment.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended, to mean an inclusive "or" rather than an exclusive "or". That is, unless specified otherwise, or clear from context, "X employs A or B" is intended to mean any of the natural inclusive permutations. That is, if X employs A; X employs B or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A remote, flexible device for integrity management of a Surveyed structure by discovering, identifying and monitoring of mechanical defects in metallic structures using non-contact remote magnetic tomography to sense defects in the metallic structure based on inverse magnetosstrictive (Villari) effect detection techniques: comprising:
   a. a flexible array in die form of a plurality of autonomous underwater vehicle (AUV) torpedo construction elements or pods;
   b. wherein each of foe plurality of AU V elements or pods are connected by rigid links or rigid connectors that are hinged or pivoted at one end to permit independent movement; the links allowing the array to follow a curved trajectory;
   c. wherein at least one of the plurality of AUV elements or pods contains at least three magnetic tomography method (MTM) sensors;
   d. wherein the MTM sensors are arranged within the plurality of AUV torpedo elements or pods at an angular separation on a non-perpendicular cross section of the AUV torpedo element or pod; and
   e. a processing unit for processing signals received from the MTM sensors and storing the signals for an off-line monitoring and a risk evaluation of the inspected structure.

2. The remote device of claim 1, wherein the torpedo elements have wires attached to their external surface, the wires performing a double function: to clean an internal surface of a pipeline and to protect against collisions with pipeline walls.

3. The remote flexible device of claim 1, wherein the device is located in a body of water for an external examination of a submerged pipeline for mapping structural defects.

4. The remote flexible device of claim 1, wherein each of the AUV elements or pods in the flexible array performs independent functions, comprising data storage, sensor data memory storage, odometer distance, GPS GLONASS location, or geomagnetic navigation; or
   wherein each of the AUV elements or pods in the flexible array performs independent functions, comprising data storage, sensor data memory storage, odometer distance, GPS or GLONASS location, and geomagnetic navigation.

5. The remote device of claim 1, wherein the MTM sensors are arranged within the plurality of AUV torpedo elements or pods at a 120-degree angular separation on a non-perpendicular cross section of the AUV torpedo element or pod.

6. The remote device of claim 1, further comprising a power supply system for transporting the flexible array.

7. The remote device of claim 1, wherein
   when a single one of the plurality of torpedo elements or pods contains only three MTM sensors, then those three MTM sensors are arranged within the single one of the plurality of torpedo elements or pods at 120-degree separation on a plane that is non-perpendicular to the axis of the single one of the AUV torpedo elements or pods; and
   when there are more than three MTM sensors in a single one of the plurality of torpedo elements and pods, then no two adjacent MTM sensors are separated by an angular distance greater than 120-degrees.

8. The remote flexible device of claim 1, wherein the device is located between 1 and 50 meters away from a submerged or underground pipeline for mapping structural defects.

9. The remote flexible device of claim 1, wherein the device is located at a threshold distance during mapping structural defects of a structure, and wherein the threshold distance is maximum of 15 times the diameter of the structure.

10. The remote flexible device of claim 1, further comprising a signal generator and a sensing unit for detecting said signal.

11. The remote flexible device of claim 1, wherein the device takes one or more horizontal cross sections of a structure, said cross sections corresponding to a slice of said structure made perpendicular to a trajectory of the device.

12. The remote flexible device of claim 1, wherein the device utilizes a unified signal which is emitted, transmitted, and detected by all MTM sensors.

13. The remote flexible device of claim 1, further comprising one or more signal generators, wherein the one or more signal generators generates two or more signals, the characteristics of the two or more signals being identical to each other, and wherein a known distance between each of the signal generators and the MTM sensors is utilized to calculate a position of each pod or element.

14. The remote device of claim 1, wherein the MTM sensors are arranged ti within the plurality of AIN torpedo elements or pods at a 120-degree angular separation on a plane, said plane being defined by the MTM sensors, said plane being non-perpendicular to a trajectory of the device.

15. The remote device of claim 1 wherein
   when a single one of the plurality of torpedo elements or pods contains only three MTM sensors, then those three MTM sensors are arranged within the single one of the plurality of torpedo elements or pods at a 120-degree separation on a non-perpendicular cross sectional plane of the single one of the plurality of AUV torpedo elements or pods; and
   when there are more than three MTM sensors in a single one of the plurality of torpedo elements and pods, then no two adjacent MTM sensors are separated by an angular distance greater than 120-degrees.

16. The remote device of claim 1, wherein the flexible array in the of a plurality of autonomous underwater vehicle (AUV) torpedo construction elements or pods is a linear array, and wherein the plurality of autonomous underwater vehicle (AUV) torpedo construction elements or pods are connected end to end.

17. The remote device of claim 1, wherein each one of the plurality of AUV elements or pods contains at least three magnetic tomography method (MTM) sensors and wherein said processing unit further compares for accuracy measurements of the at least three magnetic tomography method (MTM) sensors from each of the plurality of AUV elements or pods.

18. The remote device of claim 1, wherein a distance between the plurality of AUV elements or pods is known and only a lead AUV element or pod has a signal emitter, the processing unit taking in signals received by the at least three magnetic tomography method (MTM) sensors from each of the plurality of AU V elements or pods, and the processing unit using the known distance between the plurality of AUV elements or pods to determine a location of a defect in the metallic structure.

19. The remote device of claim 1, wherein the MTM sensors are arranged within a one or more AUV torpedo elements or pods such that at least three MTM sensors define a plane, the defined plane corresponding to a non-perpendicular cross section of the one or more AUV torpedo elements or pods.

20. The remote flexible device of claim 1, wherein the device is located within a submerged or underground pipeline for mapping structural defects.

21. The remote device of claim 20, wherein the flexible array is propelled by a motive engine.

22. The remote device of claim 20, wherein the links allow the array to turn up to 90 degrees.

23. A method for integrity survey examination of underwater, undersea or underground pipeline structures for discovering, identifying and monitoring of mechanical defects in metallic structures using non-contact remote magnetic tomography to sense defects in the metallic structure based on inverse magnetostrictive (Villari) effect detection techniques, comprising;
   a. deploying a flexible array of a plurality of autonomous undersea vehicle (ACJV) torpedo elements or pods connected by rigid links or rigid connectors that are hinged or pivoted at one end;
   b. wherein at least one of the plurality of AUV torpedo elements or pods in the deployed flexible array is coupled with at least three magnetic tomography method (MTM) sensors;
   c. wherein three or more MTM sensors are positioned such that no two adjacent MTM sensors have an angular separation than;
   d. wherein the MTM sensors are arranged within the plurality of AUV torpedo elements or pods at an angular separation on a non-perpendicular cross section of the AUV torpedo element or pod;
   e. wherein the MTM sensors receive a plurality of signals from the Earth's magnetic field, die Earth's magnetic field producing a Villari effect; and
   f. converting the plurality of MTM signals for mapping pipeline defect distribution along the length of the pipeline structure.

24. The method of claim 23, wherein the plurality of AUV torpedo elements or pods each perform independent functions, comprising data storage, sensor data memory storage, odometer distance, and GPS or GLONASS location.

25. The method of claim 23, wherein the links allow for turns up to 90 degrees in the array motion.

* * * * *